United States Patent [19]

Ponsford et al.

[11] Patent Number: 5,799,626
[45] Date of Patent: Sep. 1, 1998

[54] METHODS FOR USING STYRENE OIL (AS HEAT TRANSFER FLUID, HYDRAULIC FLUID, LUBRICANT)

[76] Inventors: Thomas E. Ponsford; Henry T. Ponsford, both of 14112 Durhullen Dr., Poway, Calif. 92064

[21] Appl. No.: 420,236

[22] Filed: Apr. 11, 1995

Related U.S. Application Data

[63] Continuation-in-part of Ser. No. 10,350, Jan. 28, 1993, Pat. No. 5,406,010.

[51] Int. Cl.⁶ .................. F01P 3/00; C07C 4/04
[52] U.S. Cl. .......... 123/41.42; 585/241; 123/1 R; 123/1 A; 60/721; 73/732; 92/261; 252/68; 252/73
[58] Field of Search .................. 60/721; 73/732; 92/261; 123/1 R, 1 A, 41.42; 252/68, 73; 585/241

[56] References Cited

U.S. PATENT DOCUMENTS

| | | |
|---|---|---|
| 2,372,528 | 3/1945 | Soday . |
| 2,383,922 | 8/1945 | Soday . |
| 3,447,914 | 6/1969 | Peterson et al. . |
| 3,467,723 | 9/1969 | Matsumoto . |
| 3,883,624 | 5/1975 | McKenzie et al. . |
| 3,903,001 | 9/1975 | Gates et al. . |
| 3,968,723 | 7/1976 | Flaterman et al. . |
| 4,057,442 | 11/1977 | Shaw et al. . |
| 4,098,627 | 7/1978 | Tompa . |
| 4,166,723 | 9/1979 | Steigelmann et al. . |
| 4,642,401 | 2/1987 | Coenen . |
| 4,790,961 | 12/1988 | Weiss et al. . |
| 5,060,870 | 10/1991 | Trezek et al. . |
| 5,070,109 | 12/1991 | Ulick et al. . |
| 5,072,068 | 12/1991 | Luo et al. . |
| 5,079,385 | 1/1992 | Wu . |
| 5,288,934 | 2/1994 | de Broqueville . |

Primary Examiner—Noah P. Kamen
Attorney, Agent, or Firm—Banner & Witcoff, Ltd.

[57] ABSTRACT

Methods of using styrene oil, its fractions, and combinations thereof as working fluids, lubricants, fuels and solvents.

46 Claims, 3 Drawing Sheets

METHODS FOR USING STYRENE OIL (AS HEAT TRANSFER FLUID, HYDRAULIC FLUID, LUBRICANT)

This application is a continuation-in-part of U.S. application Ser. No. 08/010,350, filed Jan. 28, 1993, now U.S. Pat. No. 5,406,010 which is hereby incorporated by reference in its entirety.

The invention relates generally to methods for using depolymerized styrene products and combinations thereof.

BACKGROUND OF THE INVENTION

Efforts to isolate styrene or to depolymerize polystyrene have produced a number of byproducts that have not been disclosed to have commercial utility. In 1945, Soday was awarded two U.S. Pat. Nos. 2,372,528 and 2,383,922, that disclose methods of producing styrene, a scarce commodity at that time, from low quality materials such as coal gas concentrate. Soday's process comprises the polymerization of styrene in crude naphtha, removing the unpolymerized material and replacing it with a high boiling solvent, and then depolymerizing the polystyrene to styrene by rapidly heating the solution to a temperature of about 600° C. Soday made vigorous efforts to minimize the amount of the "undesirable high boiling point oils," as he repeatedly called them, which were produced as a byproduct of his process. He saw them only as a reduction in the yield of the styrene monomer which he desired, and discarded them from his process.

U.S. Pat. No. 5,288,934 to de Broqueville discloses a process to reclaim mixed polymer, including polystyrene packaging waste, by grinding the material into pellets; selectively solubilizing fractions having different specific gravities; removing the solvent; and catalytically cracking the polymeric residue into lower molecular weight products. Styrene is recovered, and the residue, comprising higher boiling hydrocarbons, is recycled for further treatment. Like Soday, de Broqueville saw no commercial market for his higher boiling hydrocarbons, and does not disclose their content.

BRIEF DESCRIPTION OF THE DRAWINGS

FIG. 4 provides schematic drawings of the cooling systems for nuclear reactors.

SUMMARY OF THE INVENTION

Figure 1:
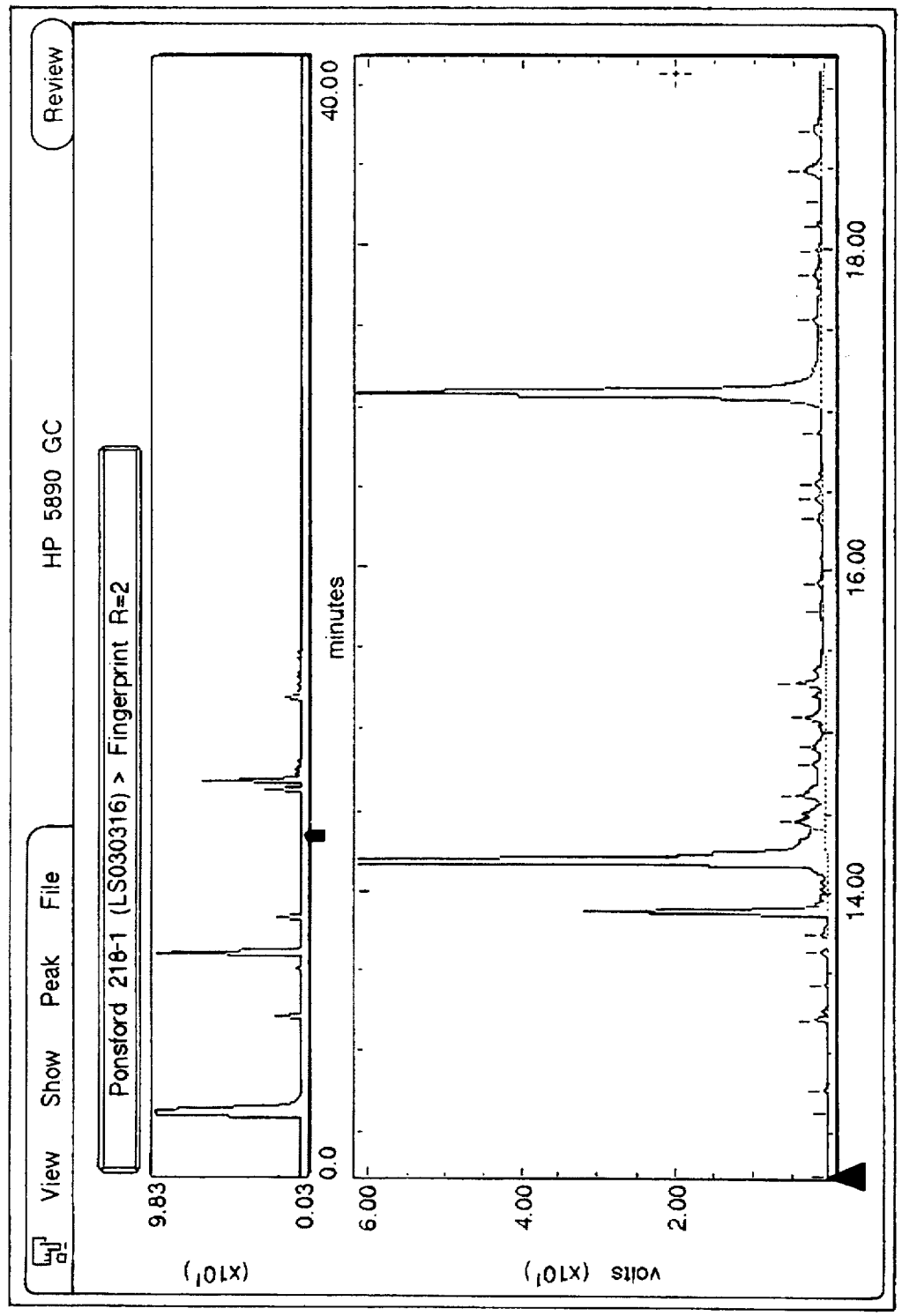
FIG. 1 is a gas chromatographic analysis of crude polystyrene distillate (styrene oil).

The invention provides improvements in a machinery system including at least a first working fluid for purposes of transferring energy, the improvement comprising styrene oil as said first working fluid. In one embodiment of this aspect of the invention the energy is thermal energy which said styrene oil absorbs. In a preferred embodiment the styrene oil absorbs thermal energy at least at a temperature within the range of about −100° C. to about 450° C. In a related embodiment of this aspect of the invention, the machinery system additionally comprises a second working fluid which is thermally coupled with the styrene oil, the thermal energy being exchanged between the styrene oil and the second working fluid. The styrene oil is a heat sink, or alternatively the styrene oil is a heat source. In yet another embodiment of this aspect of the invention, the styrene oil transfers heat to the second working fluid which has a lower boiling temperature than the styrene oil. The improved machinery system can also comprise at least a second and a third working fluid, wherein the styrene working fluid absorbs thermal energy from the second working fluid and transfers thermal energy to the third working fluid. According to yet another aspect of the invention, the machinery system is part of a chemical processing or oil refining process.

According to another aspect of the invention, the machinery system additionally comprises a radiator in which the styrene oil functions as a coolant flowing through the radiator. The machinery system can additionally comprise a combustion chamber with a coolant jacket which at least partially surrounds the chamber, the styrene oil flowing through the jacket and absorbing thermal energy from the combustion chamber to cool the combustion chamber.

According to another embodiment of this aspect of the invention, the combustion chamber forms part of an internal combustion engine. The internal combustion engine may be selected from the group consisting of a compression-ignition engine, a spark-ignition engine, and a gas turbine engine. In a preferred embodiment of this aspect of the invention, the thermal energy transfer from the styrene oil to the second working fluid is sufficient to boil the second working fluid. According to this embodiment, the second working fluid drives a turbine or piston engine. In a particularly preferred embodiment, the turbine or piston forms part of a Brayton or Rankine cycle type engine. Alternatively, the styrene oil functions as a heat source for a Stirling cycle engine.

According to another aspect of the invention, the machinery system is one in which the energy is kinetic energy or pressure energy which is transferred through the styrene oil. In yet another embodiment, the machinery system can additionally comprise a fluid coupler filled with said styrene oil. In a preferred embodiment, the fluid coupler forms a portion of a brake system. Alternatively, the fluid coupler forms a portion of a hydraulic system and is coupled to a hydraulic piston to drive the hydraulic piston.

The invention also provides a method of operating an internal combustion engine having at least one internal combustion chamber and an output device, the method comprising the steps of providing styrene oil as a fuel source; and burning said styrene oil within a combustion chamber of the engine to drive the engine output device. In particularly preferred embodiments the method produces thermal energy in a gas turbine engine or a boiler by burning styrene oil.

According to yet another aspect of the invention, there is provided an improvement in a mechanical system including a lubricant, the improvement comprising styrene oil as the lubricant, or as a lubricant additive. In a preferred embodiment, the system operates in a temperature range within about 150° C. and 400° C. Alternatively, the system operates in a temperature range within about −100° C. and 20° C.

According to yet another aspect of the invention there is provided an improvement in a cooling system for a nuclear reactor comprising a water coolant loop, the improvement comprising a styrene oil coolant loop to transfer heat from the reactor to the water. In another embodiment of this aspect of the invention there is provided a cooling system for a nuclear reactor comprising a liquid sodium coolant loop that transfers heat to a water coolant loop, the improvement comprising a styrene oil coolant loop to transfer heat from the liquid sodium to the water.

The invention further provides an auxiliary cooling system for a water cooled nuclear reactor comprising a volume of styrene oil connected by piping and a pump to the water coolant loop of said nuclear reactor. There is also provided an auxiliary cooling system for a sodium cooled nuclear reactor comprising a volume of styrene oil connected by piping and a pump to the sodium coolant loop of the nuclear reactor.

According to yet another aspect of the invention there is provided an improvement in a temperature measuring device including a fluid for purposes of detecting changes in temperature as contraction or expansion thereof, the improvement comprising styrene oil as the fluid.

The invention further provides an improved composition comprising organic or aromatic organic heat transfer fluids, the improvement comprising styrene oil admixed with the fluids. In a preferred embodiment of this aspect of the invention the concentration of styrene oil is from about 1% to about 99%.

In other embodiments, the invention further provides a composition comprising styrene monomer and an effective polymerization-inhibiting concentration of styrene oil. Also provided are compositions comprising an organic compound and a solvent system comprising styrene oil. In a preferred embodiment of this aspect of the invention, the organic compound is an aromatic compound is selected from the group consisting of benzene, toluene, styrene, polystyrene and xylene.

According to yet another aspect of the invention there is provided a method for decomposing napalm by combustion comprising the steps of optionally dissolving the napalm to be combusted together with the contained solid polystyrene in an amount of styrene oil sufficient to thin the napalm to a pumpable viscosity; heating a quantity of said napalm in a pressurized chamber that is heated to the decomposition point of polystyrene for a period of time sufficient to at least partially depolymerize the polystyrene contained in said napalm B to styrene oil, whereby the styrene oil of the decomposition products at least solubilizes the remaining polystyrene and polystyrene decomposition products; maintaining said chamber at a pressure that is sufficient to prevent boiling of the styrene oil-solubilized polystyrene and polystyrene decomposition product mixture; vaporizing the polystyrene decomposition products by expansion through an orifice of said chamber to atmospheric pressure; and burning the vaporized polystyrene decomposition product mixture.

In a preferred embodiment of this aspect of the invention, the vaporized decomposition products are burned in air as a fuel. Alternatively, the vaporized decomposition products are premixed with air and then burned as a fuel.

According to yet another embodiment of the invention, there is provided an improved method for decomposing napalm by combustion, the improvement comprising diluting the napalm with styrene oil prior to combustion. In a preferred embodiment of this aspect of the invention, the diluted napalm is a pourable, pumpable or sprayable liquid.

The invention further provides a method for inhibiting rust or corrosion of a metal part of a mechanical system comprising the application of an effective corrosion-inhibiting amount of styrene oil to the surface of said part. In a related embodiment, the invention provides a method for dissolving sludge by contacting the sludge with styrene oil. The invention further provides an improved chemical process including a working fluid as a solvent, the improvement comprising styrene oil as said solvent.

According to another aspect of the invention there are provided fractions or portions of the distillate from depolymerized polystyrene, including an isolated fraction of styrene oil, having a boiling point at atmospheric pressure of about 290° C.; an isolated fraction of styrene oil, having a boiling point at atmospheric pressure of about 305° C.; and an isolated fraction of styrene oil, having a boiling point at atmospheric pressure of about 400° C.

The invention further provides various useful applications of styrene oil, including, for example, its use as a working fluid in a pressure gauge, as a working fluid to transfer heat to a thermoelectric device, and as a carburetor cleaner and degreaser.

DETAILED DESCRIPTION OF THE INVENTION

We have developed a process for the thermal or thermal/catalytic decomposition of polystyrene that depolymerizes substantially all of the polystyrene to liquids, and produces essentially no gases, solids or char, and only 1% tar. The products of depolymerization are styrene monomer, toluene and another mixture defined herein as "styrene oil," that comprises a mixture of about 20 high-boiling point, relatively non-toxic organic compounds derived, it is believed, from incompletely depolymerized polystyrene.

The process for depolymerization is disclosed in U.S. application Ser. No. 08/010,350, now U.S. Pat. No. 5,406,010, which is hereby incorporated in its entirety. The mixture of compounds that we call styrene oil is made by thermal decomposition of polystyrene plastic in the absence of air. Polystyrene plastic is heated under one atmosphere of pressure to a temperature of approximately 350° C., when it begins to depolymerize, giving off a vapor. As the temperature is slowly increased, more polystyrene depolymerizes, continuing to produce a vapor, until at about 400° C., when depolymerization and vaporizing of the polystyrene is complete. The duration of the heating process is highly variable and can be as short as 5 to 10 minutes for small batches or as long as several hours. This process can be performed starting with pure polystyrene, or with polystyrene that is dissolved in solvents such as previously prepared styrene oil, as defined in the following paragraphs.

The polystyrene is then placed in a "cooker" and depolymerized into crude styrene distillate (a mixture which contains styrene, toluene, and styrene oil). The crude styrene distillate is then fractionally distilled at a temperature range of about 110° C. to 420° C. to separate the products.

The styrene oil is, itself, a solvent for polystyrene and an inhibitor of styrene repolymerization, and a mix of 1½ parts styrene oil to 1 part polystyrene forms a convenient solution for the depolymerization process, which can be carried out in a feedback operation wherein the styrene oil product is cycled back to process additional polystyrene.

If the vapor produced is put through a condenser, the resulting liquid is found to contain roughly 20 different compounds. Approximately 67% by weight is styrene monomer, 3% is toluene, and, significantly, less than 0.1% is benzene. Most of the remaining 30% is composed of three unusual compounds which have not as yet been identified by standard organic references. In addition, trace amounts of roughly 15 other compounds are present. The mixture of compounds which remains, that boils between approximately 250° C. and 450° C., has collectively been designated as styrene oil. A gas chromatograph analysis for the vapor produced from polystyrene is shown in FIG. 1.

The proportion of products stated is not exact, as it is known that varying the conditions under which depolymerization occurs can affect the product. Rapid heating to very high temperatures slightly increases the yield of styrene monomer, as well as possibly affecting the composition of the remaining substances in the styrene oil. It has been found that the output of styrene oil from the depolymerization process can be altered as a percentage of the total polystyrene both by the use of catalysts, and by varying the rate of depolymerization with time. Manganese oxide and copper are two such catalysts. By the use of effective catalysts and process conditions, the production of styrene monomer can be increased to nearly 100% and the production of styrene oil reduced to a negligible amount, if desired; alternatively, the process can be adjusted to produce a greater quantity of styrene oil.

The Physical and Chemical Characteristics of Styrene Oil and its Fractions

The mixture of aromatic hydrocarbon compounds called styrene oil herein is a liquid at room temperature, and physically resembles diesel oil in appearance, varying in color from light yellow to brown, depending on the presence of trace compounds. It is roughly similar to light oils in viscosity and boiling point, and is useful for many purposes as disclosed herein. Styrene oil is a material with an unusual combination of properties, and appears to be chemically stable. It does not repolymerize or thicken during storage periods greater than one year. The styrene oil mixture has little odor and a very high flash point at least above 125° C. It has a remarkably wide liquid range for an aromatic substance, having a pour point below −50° C. and a boiling point above 300° C. The specific gravity is 1.00 at room temperature and 0.94° at about 100° C. It distills to dryness at approximately 420° C. During boiling the mixture will not self-ignite in air, and when used as a fuel oil, the burner must pre-mix the styrene oil mixture as a vapor with hot air to ensure smokeless burning.

A gas chromatographic analysis of styrene oil, as shown in FIG. 1, reveals three unusual principal compounds, which boil at about 290° C., 305° C., and 400° C., and the 15–20 trace compounds indicated above. Two of the principal compounds are about equally present, and the one that boils at 290° C. is somewhat less prevalent. An extensive search through the literature for aromatic compounds with properties in the vicinity of the three cited compounds of styrene oil did not locate any matches. It appears that the two compounds that boil at 290° C. and 305° C. have molecular weights approximating that of the styrene dimer and the fraction that boils at 400° C. approximates the trimer, although their properties are very different. Once formed from depolymerization, the three principal compounds do not depolymerize on later heating, but boil without dissociation. On prolonged storage, the styrene oil shows no tendency to spontaneously polymerize, unlike the behavior of the styrene monomer.

Figure 2:
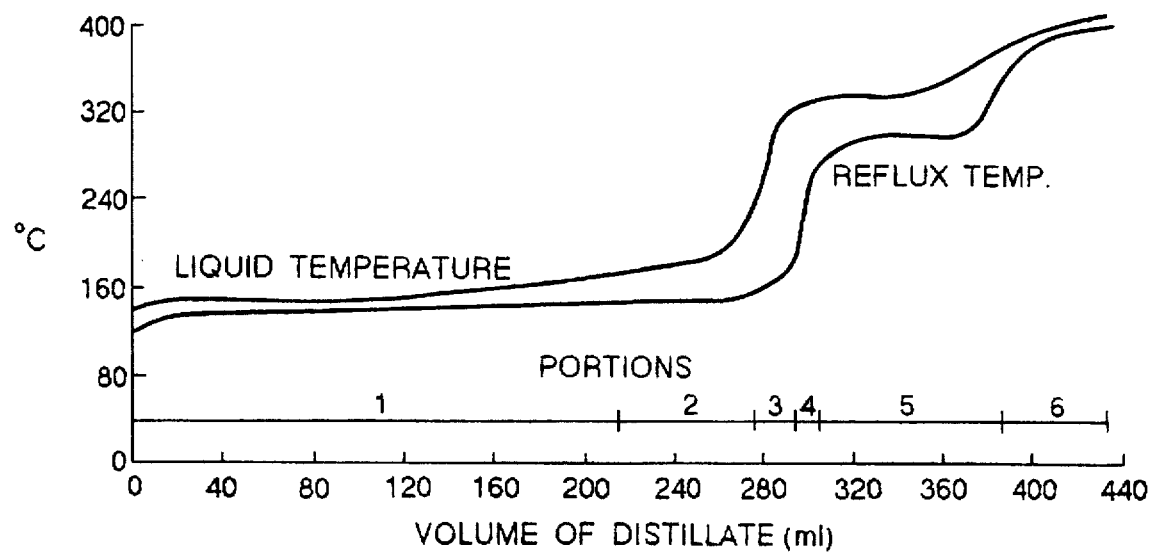
FIG. 2 is a plot of temperature vs. distillate yield for the distillation of crude styrene oil.
Figure 3:
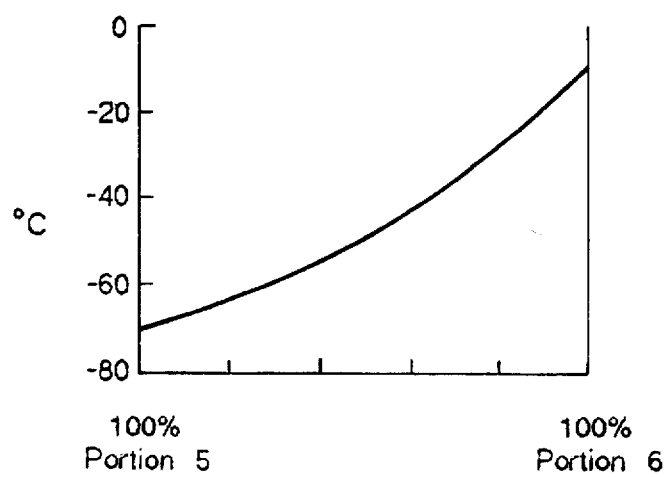
FIG. 3 shows the minimum pour temperatures of mixtures of the two highest boiling point portions of styrene oil.

As previously described, FIG. 1 shows a gas chromatograph of the distillates from a thermal decomposition of polystyrene. In order to investigate the freezing points of various parts of styrene oil, a special distillation was performed. FIG. 2 shows a perspective of the distillation, in which the distillation temperature is plotted against the amount of distillate. The distillate was collected in six portions, as shown on the figure. Table 1 shows the freezing temperature or minimum pour temperature, whichever is appropriate, of each of the six portions. FIG. 3 shows the pour temperature of mixtures of various ratios between Portion 5 and Portion 6. An interpretation of these data follows.

TABLE 1

FREEZING OR POUR TEMPERATURES OF SIX PORTIONS OF THE DISTILLATES OF FIG. 3

| Portion No. | Vol (ml)* | |
|---|---|---|
| | | Freezing Temperature (°C.) |
| 1 | 0 to 214 | −32 |
| 2 | 214 to 277 | −32 |
| 3 | 277 to 296 | −40 |
| | | Minimum Pour Temperature (°C.) |
| 4 | 296 to 306 | −95 |
| 5 | 306 to 387 | −70 |
| 6 | 387 to 434 | −10 |

*beginning and end point of total collection volume (ml)

The gas chromatograph of FIG. 1 shows clearly the presence of the three principal compounds of styrene oil, with boiling points previously cited at 290° C., 305° C. and 400° C. Portions 4–6 of the distillates were intended to capture these three compounds, respectively. Because of the close proximity of the boiling points, however, there may be some overlap. Standard references indicate that Portions 1, 2 and 3 are mostly styrene, which is consistent with the shape of the curve in FIG. 2. In addition, these three portions had definite freezing points. Portion 4 had the remarkably low pour point of −95° C. At roughly 5 degrees above this temperature, the material has the viscosity of a motor oil at room temperature; at roughly 5 degrees below, it has the viscosity of thick honey. The temperatures were those of the cooling bath in which the samples were immersed, measured with an accurate laboratory thermometer when the temperature was rising after a soak at a lower temperature. Portion 5 has a slightly higher pour point of −75° C., which might be caused by its slightly higher molecular weight, or Portion 4 may be a eutectic of styrene and Portion 5. Portion 6 had a higher pour temperature. Mixtures between Portions 5 and 6 were investigated to see if a eutectic exists between them, but FIG. 3 shows that it does not. The density at room temperature of the natural mix of Portions 1 through 6 is 0.932 gm/ml, of Portion 5 is 0.98 grams/ml, and of Portion 6 is 1.02 gm/ml.

Basic or "natural" styrene oil is a diverse mixture of compounds produced by thermal or thermal/catalytic depolymerization of polystyrene plastic at elevated temperatures, but preferably from 300° C. to 450° C. It includes molecules containing from 2 to 4 aromatic rings. Its three principal compounds boil at 290° C. and 305° C. (2 aromatic rings) and 400° C. (three aromatic rings), plus about 15 minor compounds. According to the invention, however, we use a broader generic definition. Styrene oil is defined generically as the natural mixture of compounds present in the original production of styrene oil, or as each individual compound produced in the original production, or as mixtures of the original compounds in ratios different from the natural blend, or as mixtures of the compounds of styrene oil with other compounds not present in the natural styrene oil, in any mixture ratios. In addition, the generic definition includes styrene oil modified by hydrogenation of any unsaturated bonds in its molecules, including but not limited to alkene bonds, and hydrogenation of aromatic rings to naphthenic rings.

The ability of light styrene oil fraction (Portion 5) to reduce potassium permanganate is 1/12 of that of pure styrene monomer by weight, implying a higher degree of saturation in styrene oil.

Styrene oil is a very good solvent of other aromatic hydrocarbons, as well as other organic compounds. At room temperature, it will dissolve benzene, toluene, styrene, xylene, methyl ethyl ketone, acetone, ethyl acetate and 1-1-1-trichloroethane in any proportions and is a very good solvent of polystyrene. Portion 5 is less than 2% soluble in methyl alcohol, 40% soluble in ethyl alcohol, and infinitely soluble in isopropyl alcohol. Portion 5 is less than 2% soluble in all those cited alcohols. Styrene oil is almost insoluble in water.

Styrene oil has other unusual properties. It is a good lubricant over a wide range of temperatures, from about −100° C. to about 400° C. It has an unusually low variation in viscosity with temperature over the same wide range, having a significantly lower variation of viscosity with temperature than typical "all-weather" motor oils. It is an excellent rust inhibitor for iron and steel, and is a very good anti-seize compound. It does not damage silicone seals on years of exposure or on prolonged exposure at 400° C. Furthermore, silicone seals compressed in contact with steel and exposed to styrene oil at 400° C. will not adhere to the steel, only a small amount of styrene oil will prevent styrene monomer from spontaneously polymerizing in storage for several years.

Styrene oil has two characteristics which make it a safe material to use. Although its toxicity has not yet been measured by rigorous biological testing, it has been used in free contact with humans for over five years with no evidence of toxic or allergic effect. There have been no sinus problems, skin problems, headaches or unexplained illness symptoms of any type. Its large molecular weight and chemical stability probably make styrene oil incompatible with biological functions. The other characteristic contributing to its safety is its very high spontaneous ignition temperature, which is well over 400° C. In all of the laboratory test work with styrene oil carried out in the reduction to practice of the present invention, there has never been a flash fire. This characteristic means that accidental emissions of hot styrene oil from working machinery, for example, a broken pipe joint, will not produce a fire in air by itself, or in contact with hot metal compounds.

Another favorable property of styrene oil is the manner of its deterioration on being subjected to high temperatures for a long time. The low boilers released from styrene oil are mostly toluene, a relatively benign chemical. The fact that benzene is not produced is proved by the absence of benzene during the original production of styrene oil. Other chemicals now used in industry at high temperatures for a long time release benzene, a much more toxic low boiler, and a known carcinogen.

Portion 5 of the styrene oil has a very low pour point (−70° C.), and its viscosity and heat transfer properties are very good down to about −60° C. It is non-corrosive to all metals used in refrigeration and is a good pump lubricant. It would make an excellent substitute for the corrosive brine solution (e.g., calcium chloride in water) currently used to distribute cold from a central refrigeration system to other parts of a large building. To avoid the difficulties of brine, most single family houses and apartment buildings are cooled by air conditioning systems that use the refrigerant working fluid, chlorofluorocarbons (CFC), also as the distribution agent. To transfer heat or cold into air requires a large surface area heat exchanger with a possibility of leakage of refrigerant into the atmosphere. The long lines carrying the refrigerant to and from the compressor also may leak. These leaks can release harmful CFC's to the environment, and this problem can be minimized by the use of styrene oil as the distribution agent. Liquid to liquid heat exchangers are smaller, more rugged, and less likely to leak. The cold could be exchanged from the CFC to styrene oil at the central compressor with much less chance of a refrigerant leak. In addition, it is common practice for most refrigeration systems to allow the compressed, warm refrigerant to expand through a throttle valve without performing useful work. If the refrigerant fluid is made to do work in an expansion engine, such as a small piston engine or turbine, the efficiency of the system is greatly increased. Such engines are often not used for want of a good lubricant at very low temperatures. Styrene oil would be good as an expander engine lubricant down to −60° C.

In addition, styrene oil is an effective paint stripper which has a very low vapor pressure at room temperature, thus reducing the release of smog producing chemicals into the atmosphere.

Another virtue of styrene oil is the low cost of the polystyrene scrap and waste from which it is produced as well as the economy of its production. Discarded foamed polystyrene, which is abundant, is a significant waste disposal problem of modern times.

The Uses of Styrene Oil

The unusual combination of physical properties of styrene oil make it useful as a fluid in working machinery, and provide remarkable advantages over such fluids presently in use. Styrene oil is a good lubricant which breaks down very slowly, it inhibits corrosion of iron and steel, is safe from accidental fires, has a very low pour point and a low viscosity which varies only slightly with temperature. These characteristics make it suitable, for example, as:

1. Hydraulic fluid for machinery which must operate over a wide range of temperatures.
2. Brake fluid for brakes which must operate over a wide range of temperatures.
3. High and low temperature lubricant for machinery.
4. High and low temperature fluid coupling fluid in machinery.
5. High and low temperature thermometer fluid.
6. High and low temperature pressure gauge fluid, for example, in a Bourdon tube.
7. Heat transfer fluid in chemical and oil refining processes.
8. Engine cooling fluid.
9. Working fluid for a Rankine engine.
10. Solvent for chemicals in laboratory and production operations.
11. Inhibitor of styrene polymerization.
12. Boiler fuel, gas turbine fuel, or Diesel fuel.
13. Heat transfer fluid for the transfer of heat energy to a thermoelectric element.

The above applications are not to be considered exclusive, but only as examples of preferred embodiments.

Styrene Oil as a Heat Transfer Fluid

A specialized application for which styrene oil is most suitable is as a heat transfer fluid in chemical and oil refining processes (7). Heat transfer fluids are widely used at present, and are typified by the commercially available aromatic compounds comprising the Dowtherm™ group of heat transfer fluids. One important reason why several Dowtherm™ fluids are marketed is the inability of any one fluid to cover the entire temperature range required by all potential processes of use. Dowtherm™ A, for example, is excellent at high temperatures, but freezes at +12° C. Such a high freezing temperature is very undesirable if a process should have to be shut down in cold weather, because getting the equipment entirely thawed out can be a real problem. For processes which must operate in cold weather conditions, other Dowtherm™ types are available which do not freeze in cold weather, but these cannot operate at the high temperature ranges of Dowtherm™ A. In addition, the Dowtherm™ heat transfer fluids are comparatively expensive ($2–$3/pound). Styrene oil will operate as a heat transfer fluid throughout the entire temperature range of all the Dowtherm™ fluids collectively, and at less cost. It should be noted that styrene oil as a "heat transfer fluid" is useful both for heating and for cooling purposes.

Styrene oil has a special advantage as a heat transfer fluid in its ability to give custom accommodation to the requirements of processing plants located in areas with widely varying climactic conditions. Ideally, plants desire heat transfer fluids which operate at the highest possible temperature consistent with not freezing at the lowest expected local temperature. As previously discussed concerning the Dowtherm™ fluids, the limited choices fall short of satisfying the ideal goal, as Dowtherm™ A is the only fluid which will operate at very high temperatures, but it freezes at +12° C. All of the others operate at much lower temperatures. In order to achieve the highest possible temperature consistent with chemical stability, heat transfer fluids are generally operated under pressure, as in an automobile cooling system. The two components of styrene oil which boil at 305° C. and 400° C. both appear to be stable up to 400° C., but have widely differing freezing temperatures, as shown in Table 1. The freezing temperatures of mixes of these two compounds are shown in FIG. 3. Clearly, mixtures rich in the 305° C. compound are needed in cold climates, but require stronger piping to boil at 400° C. Conversely, mixtures rich in the 400° C. compound will be suitable for plants in mild climates, and will require lower pressure piping to boil at 400° C. An example of this tradeoff follows. If a refinery is to be operated in Aruba, a fluid containing 100% of the 400° C. compound can be used, since +7° C. might be as cold as the refinery would ever experience. If a refinery were to be operated in Alaska, however, a −50° C. freezing temperature might be desired, and a mix using only 50% of the higher boiling fluid might be requested, to be contained in thicker pipes. It would be easy to mix a custom heat transfer fluid for each individual plant, closely approaching the ideal.

In other embodiments, styrene oil can be used in combination with existing aromatic compound heat transfer fluids to extend their working temperature range or to reduce the cost of materials. Styrene oil is miscible with such working fluids over the entire concentration range of from about 1% to 99% by volume of the total mixture.

The most valuable use of styrene oil is as a working fluid in conjunction with internal combustion engines, not only for existing engines such as the Diesel engine, gasoline engine (Otto cycle), and gas turbine (Brayton cycle), but also in superior engines of future design made possible by the availability of styrene oil. The ways in which styrene oil can improve an internal combustion engine are as a superior engine cooling system fluid (8), and as a working fluid for an auxiliary Rankine engine (9) which works in conjunction with the basic internal combustion engine by extracting power from the internal combustion engine exhaust gases, or both together.

As a heat transfer fluid in the engine cooling system, styrene oil has all the advantages cited in (7) above. The engine can be operated much hotter than is current practice at only one atmosphere pressure without any danger of boiling, thus insuring maximum solid to liquid heat transfer and better thermodynamic efficiency. Protection against freezing can be insured to very low temperatures. In addition, the problems of corrosion and sludge formation at high temperature in engine cooling systems are well known, and the use of styrene oil would keep the system ever clean and free flowing. In these respects, the use of styrene oil may be preferable to water in cooling systems, even though it lacks water's high specific heat and heat of vaporization.

The use of turbines driven by the exhaust gases of internal combustion engines to drive superchargers is well known. It is also well known, however, that the low molecular weight, high temperature and corrosive nature of exhaust gases create severe problems in such applications. These conditions often require either the use of expensive high alloy steels or the deliberate waste of potentially recoverable energy in order to keep the turbines from deteriorating rapidly from corrosion and the impingement of the high velocity and high temperature exhaust gas stream against the rapidly rotating turbine blades. A counterflow heat exchanger is an excellent device to transfer some of the heat of the exhaust gases to a stream of styrene oil, since there are no long temperature dwells caused by a large latent heat of vaporization in the styrene oil. The styrene oil can be heated to approximately 370° C. and then expanded into a turbine. The expanded gas will be 100% vapor phase all the way down, and moving slow enough, because of its high molecular weight, to permit the use of ordinary steel turbine blades. A considerable amount of power can be obtained with relatively simple machinery, and such a thermal system can either be added to existing engines as a retrofit, or designed integrally into future engines. In addition to driving a turbine, the heat transfer can also drive other types of Rankine engines and expanders such as piston engines. The hot styrene oil can also serve as the heat source for Stirling cycle engines, which use external heat to activate a gas working fluid, and other Brayton cycle (gas turbine) engines. Also the heat transfer fluid can supply heat to a thermoelectric element for the production of electricity or for thermoelectric refrigeration.

In future internal combustion engine designs, the opportunity exists to design an engine in which an initial cold stream of styrene oil first goes into the internal combustion engine cooling system and receives heat from an engine which is running at better efficiency than current engines because of its higher operating temperature; then goes into the exhaust gas heat exchanger and receives more heat; and then expands into a turbine running efficiently under relatively mild conditions, delivering the maximum possible energy for useful purposes. The expanded gas would then flow into a condensing radiator, and the loop repeated. Such an engine using application (8) and (9) together would surely have a thermal efficiency considerably above current Diesel engines, mechanical simplicity, and a clean, unpressurized engine cooling system, all using only a single working fluid. It would make a superior power plant for ships, railroad locomotives, heavy trucks and other uses. Naturally, considerable future mechanical design work must be done to bring such an engine to practical use, but the availability of styrene oil opens the door for such an achievement.

Styrene Oil in Nuclear Reactors

Styrene oil can be used to significantly improve the safety of nuclear reactors, both as retrofits to existing reactors, and in new designs. Devices to provide for the use of styrene oil can be retrofitted, for example, to two existing types of reactors, water-cooled and liquid sodium-cooled, as well as to modifications of the two designs for new construction. Typical designs for nuclear reactors are shown in FIG. 4.

Figure 4A:
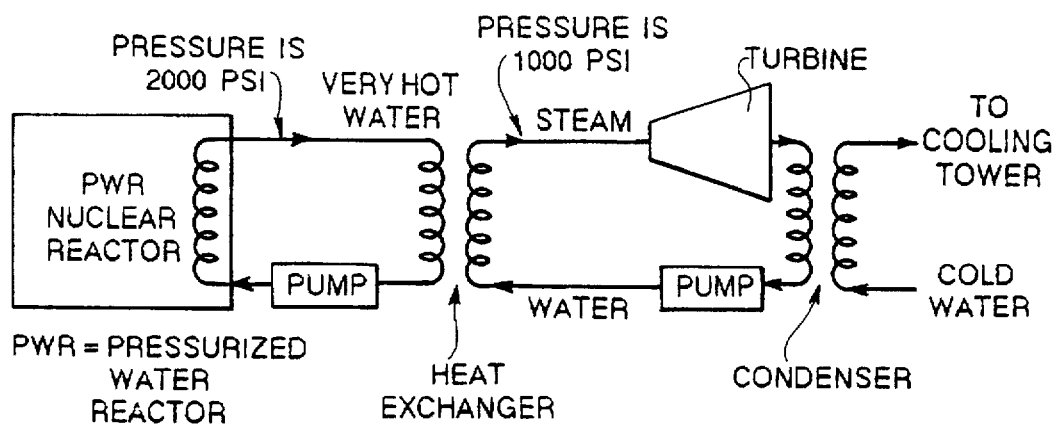
FIG. 4a shows the cooling system for a conventional pressurized water reactor.

FIG. 4a shows a schematic diagram of the cooling system of a common water-cooled reactor. This design uses two water loops to transfer heat from the reactor: a high pressure water loop to extract heat from the reactor efficiently, and a lower pressure steam loop to accept the heat from the first water loop and generate steam to drive a turbine. A hazard in this design is the potential rapid loss of water from the high pressure loop in the event of a significant leak at any point in the loop. In this event, the reactor would no longer be cooled and a rapid meltdown could occur. This possibility can be greatly mitigated in a retrofit approach by providing a large tank of styrene oil which is connected by pumps and pipes to the high pressure water loop at several places. In the event of a leak, the pumps are activated to flood the high pressure loop with styrene oil. Since styrene oil does not exert a large vapor pressure at the reactor temperature, this flooding can be done readily. The flow of oil through the reactor cools it until an orderly shutdown can be made. It is believed that styrene oil is not sensitive to radiation, and any fire resulting from leaking styrene oil can be extinguished by ordinary means.

An alternative new design of this type of reactor can use styrene oil as the original heat transfer fluid which circulates through the reactor in place of high pressure water. The styrene oil loop can operate at a much lower pressure than a liquid water loop, reducing the rate of loss of coolant in the event of a leak and easing the task of an emergency backup system to flood the loop with reserve styrene oil. Provided the styrene oil has long term radiation resistance, such a design is much safer than the current design.

Figure 4B:
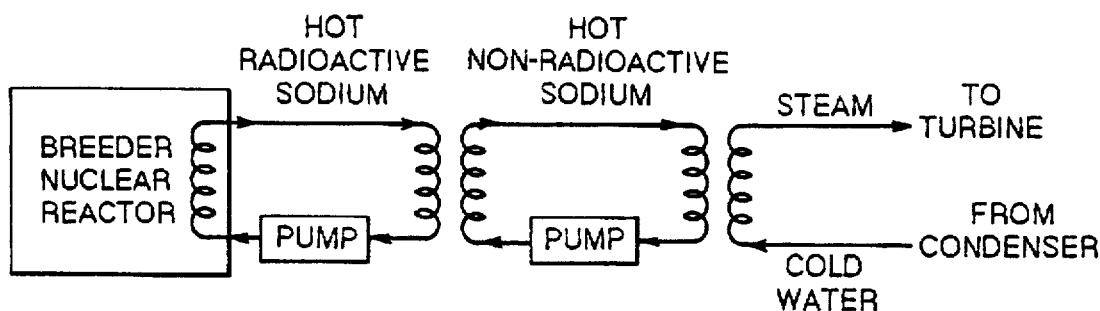
FIG. 4b shows the cooling system for a conventional sodium cooled breeder reactor.

A typical schematic of a modern liquid sodium-cooled reactor in shown in FIG. 4b. This reactor design suffers from at least two serious hazards which arise from leaks that occur in the liquid sodium loops: (1) a large leak from any cause in either of the liquid sodium loops which could lead to a significant loss of liquid sodium coolant from the radioactive sodium loop, reducing reactor cooling and causing a reactor meltdown. A large sodium fire in air can also occur. (2) a small leak in the heat exchanger between the non-radioactive liquid sodium and water loops which could allow water at high pressure to enter the liquid sodium loop, flash to steam, cause a combined steam/chemical explosion, and burst the liquid sodium pipes, with consequences similar to those of the pressurized water reactor of (1).

The consequences of both types of leaks in the breeder type reactor can be mitigated, as before, by the presence of a large tank of styrene oil which is connected by pipes and pumps to the sodium loops at several places. In the event of either type of leak above, the pumps are activated to flood the leaking sodium loop with styrene oil. Since styrene oil does not exert a large vapor pressure at the reactor temperature, this flooding can be done readily. The flow of coolant through the reactor continues until an orderly shutdown can be made. Any resulting styrene oil fire would be less severe than a sodium fire, and easier to combat using ordinary methods. In addition, the sodium smoke might be radioactive and the styrene oil smoke would not. If a small leak in the sodium/water heat exchanger is detected before a disastrous explosion occurs, the presence of styrene oil in the sodium loop will tend to keep the water and sodium separated.

Figure 4C:
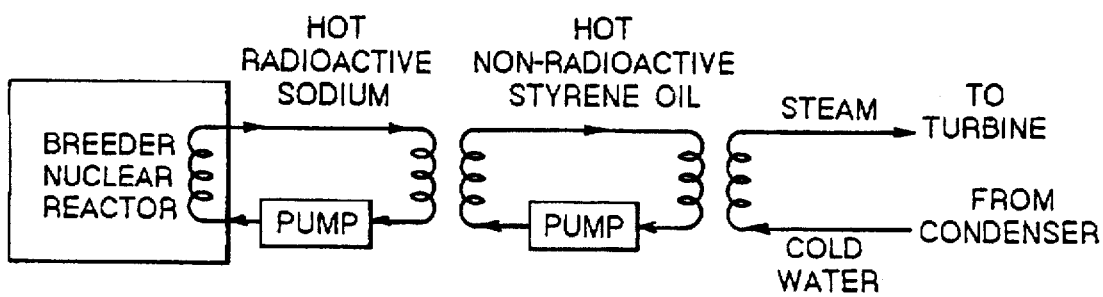
FIG. 4c shows the cooling system for the breeder reactor of FIG. 4b wherein styrene oil replaces nonradioactive sodium as a heat transfer agent in an intermediate loop.

In a new design, a safer nuclear power plant design can be made as a variation of the previous liquid sodium reactor design, by using a styrene oil loop between the liquid sodium loop and the steam loop, as shown in FIG. 4c. This design eliminates the possibility of a type (2) leak, where water and sodium could mix, from occurring. Since the most likely location for a leak to occur in the sodium loop is in the many thin walls of the heat exchanger, a considerable improvement in safety can result. Any reaction between liquid sodium and styrene oil will be much milder than with water. An emergency supply of styrene oil to protect against large leaks in the sodium loops can be provided as in the present day retrofit reactor design.

Styrene Oil as a Solvent

Styrene oil has chemical uses also. It is an excellent solvent for many aromatic hydrocarbons and other chemicals both in laboratory investigations and chemical engineering production. In the large chemical industry and laboratories which use styrene monomer, the problem of spontaneous polymerization must be guarded against. Styrene oil is an excellent inhibitor of such polymerization, and is effective at low concentrations of 1% or less even when distilling styrene at atmospheric pressure. Also in a preferred embodiment, styrene oil is used as a cleaning agent for mechanical parts, for example, as a carburetor cleaner or a parts degreaser. The vapor pressure of styrene oil at 25° C. is about 0.002 mm Hg, which reduces fumes. Styrene oil can remove rust, corrosion, sludge and chemical deposits, when used either as a cleaner or an operating fluid. Styrene oil thus used can also inhibit corrosion and rust and prevent the buildup of sludge and chemical deposits.

Styrene Oil used to Dispose of Napalm B

Styrene oil can be used to assist in the disposal of military surplus Napalm B by combustion in two different ways:

1. Styrene oil can be used to thin the Napalm B to the extent that it can be sprayed into the air and burned, as in a cement kiln or a toxic waste incinerator.

2. The napalm B can be partially thinned with styrene oil and then forced under pressure through a heated metal tube. The heat in the tube decomposes the polystyrene of the napalm B into a mixture of styrene and additional styrene oil, but the pressure in the tube is sufficient to keep the decomposition products from boiling. The mixture of liquids is then vaporized by expansion through an orifice to atmospheric pressure, and either sprayed into air and burned, or pre-mixed with air and then burned.

Styrene Oil as a Fuel

The fractions of styrene oil can be burned as a boiler fuel, gas turbine fuel or Diesel fuel if they become in surplus on the market. The aromatic styrene oil can be burned cleanly in a premixed vapor/air flame like a Bunsen burner or styrene oil can be sprayed into the air and burned.

Other uses of Styrene Oil

Styrene oil is well suited for use as a fluid in thermometer and pressure gauges, because it is liquid over a wide range of temperatures. It lacks the toxicity of mercury presently used in many thermometers and is significantly cheaper. Because of the extreme temperature advantage over other materials, it can be used in pressure gauges, such as the Bourdon type, at very high and very low temperatures.

Accordingly, the invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

What is claimed is:

1. In a mechanical system including at least a first working fluid for purposes of transferring energy, the improvement comprising styrene oil as said first working fluid.

2. The system of claim 1 wherein said energy is thermal energy which is transferred through said styrene oil.

3. The system of claim 2 wherein said styrene oil transfers said thermal energy at least at a temperature within the range of about −100° C. to about 450° C.

4. The system of claim 2 additionally comprising a second working fluid which is thermally coupled with said styrene oil, said thermal energy being exchanged between said styrene oil and said second working fluid.

5. The system of claim 4 wherein said styrene oil is a heat sink.

6. The system of claim 4 wherein said styrene oil is a heat source.

7. The system of claim 4 wherein said styrene oil transfers heat to said second working fluid which has a lower boiling temperature than said styrene oil.

8. The system of claim 7, wherein said second working fluid drives a turbine or piston engine.

9. The system of claim 8, wherein said turbine forms part of a Brayton or Rankine cycle type engine.

10. The machinery system of claim 4 wherein said styrene oil functions as a heat source for a Stirling cycle engine.

11. The system of claim 2 comprising at least a second and a third working fluid, wherein said styrene oil working fluid absorbs thermal energy from said second working fluid and transfers thermal energy to said third working fluid.

12. The system of claim 2 additionally comprising a radiator in which said styrene oil functions as a coolant flowing through said radiator.

13. The system of claim 2 additionally comprising a combustion chamber with a coolant jacket which at least partially surrounds said chamber, said styrene oil flowing through said jacket and absorbing thermal energy from said combustion chamber to cool said combustion chamber.

14. The system of claim 13, wherein said combustion chamber forms part of an internal combustion engine.

15. The system of claim 14 wherein said internal combustion engine is selected from the group consisting of a compression-ignition engine, a spark-ignition engine, and a gas turbine engine.

16. The system of claim 13 wherein said combustion chamber forms part of an external combustion engine.

17. The system of claim 2 for recovering energy from the exhaust gases of an internal combustion engine having at least one combustion chamber, further comprising an exhaust gas heat exchanger, an expansion nozzle, a turbine, a condensing radiator and a pump, said styrene oil flowing sequentially through said exhaust gas heat exchanger to absorb thermal energy from said exhaust gases, through said expansion nozzle wherein the styrene oil is vaporized, the styrene oil vapor driving said turbine, the styrene oil vapor exiting from said turbine flowing through and condensing in said radiator, and the pump returning the condensed styrene oil to said exhaust gas heat exchanger.

18. The system of claim 17 wherein said turbine produces mechanical energy which can be used to drive a supercharger for feeding the engine, or added to the drive shaft energy produced by the engine, or both.

19. The system of claim 17 wherein said engine has a coolant jacket surrounding the combustion chamber, said styrene oil flowing from said pump through said coolant jacket and then to said exhaust gas heat exchanger to absorb thermal energy from and cool said combustion chamber before recovering energy from said exhaust gases.

20. The system of claim 2 operating as a refrigeration system which uses a heat transfer fluid, wherein said styrene oil is the heat transfer fluid.

21. The system of claim 1 which is a part of a chemical processing or oil refining process.

22. The system of claim 1 wherein said energy is kinetic energy or pressure energy which is transferred through said styrene oil.

23. The system of claim 22 additionally comprising a fluid coupler filled with said styrene oil.

24. The system of claim 23, wherein said fluid coupler forms a portion of a brake system.

25. The system of claim 23 wherein said fluid coupler forms a portion of a hydraulic system and is coupled to a hydraulic piston to drive said hydraulic piston.

26. The system of claim 22 operating as an automatic transmission.

27. The system of claim 22 operating as a power steering system.

28. In a mechanical system including a lubricant, the improvement comprising styrene oil as the lubricant, or as a lubricant additive.

29. The system of claim 28 wherein said system operates in a temperature range within about 150° C. and 400° C.

30. The system of claim 28 wherein said system operates at a temperature between about −100° C. and 20° C.

31. The system of claim 28 wherein said styrene oil is effective as a lubricant from about −100° C. to about 400° C.

32. The system of claim 28 wherein said system operates in a temperature range within about −40° C. and 250° C.

33. In a composition comprising heat transfer fluids containing organic compounds the improvement comprising styrene oil admixed with said fluids.

34. The composition of claim 33 wherein the concentration of styrene oil is from about 1% to about 99%.

35. A composition comprising styrene monomer and an effective polymerization-inhibiting concentration of styrene oil.

36. A composition comprising an organic compound and a solvent system comprising styrene oil.

37. The composition of claim 36 wherein the organic compound is an aromatic compound selected from the group consisting of benzene, toluene, styrene, polystyrene and xylene.

38. A method for inhibiting rust or corrosion of a metal part of a mechanical system comprising the application of an effective corrosion-inhibiting amount of styrene oil to the surface of said part.

39. In a chemical process including a working fluid as a solvent, the improvement comprising styrene oil as said solvent.

40. An isolated fraction of styrene oil, having a boiling point at atmospheric pressure of about 290° C.

41. An isolated fraction of styrene oil, having a boiling point at atmospheric pressure of about 305° C.

42. An isolated fraction of styrene oil, having a boiling point at atmospheric pressure of about 400° C.

43. In a thermometer having a working fluid, the improvement comprising styrene oil as the working fluid.

44. In a pressure gauge having a working fluid, the improvement comprising styrene oil as the working fluid.

45. The pressure gauge of claim 44 wherein the gauge is of the Bourdon tube type, and said styrene oil fills said Bourdon tube.

46. A method of using styrene oil selected from the group consisting of:

(A) in a mechanical system, as a working fluid for transferring energy;

(B) in a mechanical system, as a working fluid for transferring thermal energy;

(C) in a refrigeration system, as a working fluid for transferring thermal energy;

(D) in a mechanical system including a combustion chamber, as a working fluid for cooling the combustion chamber;

(E) in a mechanical system including an internal combustion engine, as a working fluid for recovering energy from the exhaust gases of the engine;

(F) in a mechanical system, as a working fluid which is heated and then vaporized through an expansion nozzle to do useful work;

(G) in a mechanical system, as a working fluid for transferring kinetic energy;

(H) in a mechanical system, as a working fluid for transferring pressure energy;

(I) as a working fluid in an automatic transmission;

(J) as a working fluid in a power steering system;

(K) as a working fluid in a brake system;

(L) as a working fluid in a fluid coupler;

(M) as a working fluid in a hydraulic system to drive a hydraulic piston;

(N) as a working fluid in a pressure gauge;

(O) as a working fluid in a thermometer;

(P) as a lubricant in a mechanical system;

(Q) as a rust or corrosion inhibitor in a mechanical system;

(R) as a component of a heat transfer fluid containing organic compounds;

(S) as a polymerization inhibitor for styrene monomer;

(T) as a solvent in a chemical process.

* * * * *